United States Patent [19]
Joseph

[11] Patent Number: 5,819,723
[45] Date of Patent: *Oct. 13, 1998

[54] METHODS AND APPARATUS FOR REDUCING TRACHEAL INFECTION

[75] Inventor: Jeffrey I. Joseph, Penn Valley, Pa.

[73] Assignee: Thomas Jefferson University, Philadelphia, Pa.

[ * ] Notice: The term of this patent shall not extend beyond the expiration date of Pat. No. 5,582,167.

[21] Appl. No.: 702,676

[22] PCT Filed: Mar. 1, 1995

[86] PCT No.: PCT/US95/01904

§ 371 Date: Aug. 30, 1996

§ 102(e) Date: Aug. 30, 1996

[87] PCT Pub. No.: WO95/23624

PCT Pub. Date: Sep. 8, 1995

Related U.S. Application Data

[63] Continuation-in-part of Ser. No. 204,481, Mar. 2, 1994, Pat. No. 5,582,167.

[51] Int. Cl.⁶ .................................................. A61M 16/00
[52] U.S. Cl. .............................. 128/207.14; 128/207.15; 128/202.22; 604/97
[58] Field of Search ........................ 128/207.14, 207.15, 128/202.22; 604/97, 98, 103

[56] References Cited

U.S. PATENT DOCUMENTS

| | | | |
|---|---|---|---|
| 2,854,982 | 10/1958 | Pagano | 604/101 |
| 3,593,713 | 7/1971 | Bogoff | 604/96 |
| 4,305,392 | 12/1981 | Chester | 128/207.15 |
| 4,327,721 | 5/1982 | Goldin et al. | 128/207.15 |
| 4,334,534 | 6/1982 | Ozaki | 128/207.15 |
| 4,468,216 | 8/1984 | Muto | 604/43 |
| 4,584,998 | 4/1986 | McGrail | 128/207.15 |
| 4,607,635 | 8/1986 | Heyden | 128/207.15 |

(List continued on next page.)

OTHER PUBLICATIONS

Morris, et al., "An Electropneumatic Instrument For Measuring And Controlling The Pressures In The Cuffs of Tracheal Tubes: 'The Cardiff Cuff Controller'," *J. Med. Eng. & Tech.*, vol. 9, No. 5 (Sep./Oct. 1985), pp. 229–230.

Cobley, et al., "Endobronchial Cuff Pressures," *British J. Anesthesia*, 70:576–78 (1993).

Willis, et al., "Tracheal Tube Cuff Pressure: Clinical Use Of The Cardiff Cuff Controller," *Anaesthesia*, 43:312–14 (1988).

Spray, et al., "Aspiration Pneumonia: Incidence of Aspiration with Endotracheal Tubes," *Am. J. Surg.*, 131:701–03 (Jun., 1976).

Mahul, et al., "Prevention of nosocomial pneumonia in intubated patients: respective role of mechanical suglottic secretions drainage and stress ulcer prophylaxis," *Intensive Care Med.*, 18:20–25 (1992).

*Primary Examiner*—V. Millin
*Assistant Examiner*—William J. Deane, Jr.
*Attorney, Agent, or Firm*—Woodcock Washburn Kurtz Mackiewicz & Norris, LLP

[57] ABSTRACT

An integrated system providing a mechanical and chemical barrier against the spread of infected secretions into the distal trachea is disclosed. An endotracheal tube is used for patient airway management and provides a means to conveniently irrigate and drain the subglottic region below the vocal cords and above an inflated cuff. The subglottic region accumulates liquid secretions that may channel past an inflated endotracheal tube cuff, providing the necessary bacterial inoculum leading to bronchitis and nosocomial pneumonia. An irrigation channel delivers liquids such as saline or antibiotic and antifungal medications for mucosal hydration, and bactericidal action against infected subglottic secretions. An outer sleeve surrounding the endotracheal tube forms a suction lumen for removing the secretions. Electronic and mechanical controls provide regulated volume infusion and regulated suction.

45 Claims, 3 Drawing Sheets

U.S. PATENT DOCUMENTS

| | | | |
|---|---|---|---|
| 4,632,108 | 12/1986 | Geil | 128/207.15 |
| 4,637,389 | 1/1987 | Heyden | 128/207.15 |
| 4,693,243 | 9/1987 | Buras | 128/207.15 |
| 4,762,125 | 8/1988 | Leiman et al. | 128/207.15 |
| 4,770,170 | 9/1988 | Sato et al. | 128/207.15 |
| 4,825,862 | 5/1989 | Sato et al. | 128/207.15 |
| 4,924,862 | 5/1990 | Levinson | 128/207.16 |
| 4,955,375 | 9/1990 | Martinez | 128/207.15 |
| 4,976,261 | 12/1990 | Gluck et al. | 128/207.15 |
| 4,977,894 | 12/1990 | Davies | 128/207.15 |
| 5,067,497 | 11/1991 | Greear et al. | 128/207.15 |
| 5,143,062 | 9/1992 | Peckham | 128/207.15 |
| 5,146,916 | 9/1992 | Catalani | 128/207.15 |
| 5,235,973 | 8/1993 | Levinson | 128/207.15 |
| 5,311,864 | 5/1994 | Huerta | 128/207.15 |
| 5,361,753 | 11/1994 | Pothmann et al. | 128/202.22 |
| 5,372,131 | 12/1994 | Heinen, Jr. | 128/207.15 |

METHODS AND APPARATUS FOR REDUCING TRACHEAL INFECTION

This application, which was filed under 35 U.S.C. §371 on Mar. 1, 1995 as International Application Serial No. PCT/US95/01904, is a continuation-in part of application Ser. No. 08/204,481, filed Mar. 2, 1994, now U.S. Pat. No. 5,582,167.

The present invention relates to tracheal tubes, and more specifically, relates to methods and apparatus for controlling the conditions of the intubation.

BACKGROUND OF THE INVENTION

Tracheal intubation is used in respiratory medicine to deliver or remove a fluid to the airways of a patient. Tracheal intubation with an endotracheal tube is commonly used during general anesthesia and when critically ill patients require airway protection and mechanical ventilation. Tracheal tubes include those used in tracheostomies as well as endotracheal tubes. Under certain conditions of long term ventilation, a tracheostomy tube is inserted through a surgical opening through the neck. An endotracheal tube is inserted into the trachea through either the mouth or nose (nasotracheal tube). Tracheal tubes are used for ventilation, and removal of secretions. Typically, endotracheal tubes are disposable plastic tubes, easily placed through the mouth or nose, that guarantee a patent conduit for the delivery of respiratory gases. A seal between the outer wall of the tracheal tube and the inner lining of the trachea (the tracheal mucosa) must be formed. Most endotracheal tubes (except those for small children) provide a very compliant, thin walled inflatable cuff that forms a seal with the proximal tracheal rings. This seal allows for positive pressure ventilation at normal airway pressures with minimal leakage. The seal thus provides a closed circuit for ventilation and also prevents aspiration of pharyngeal contents into the respiratory tract. This seal is usually formed by inflating a pressurized cuff that surrounds the tracheal tube. The pressure in the cuff must be adequate to form a seal, but it is known that over-pressurization will cause tracheal trauma including hemorrhage, ulcers, perforation and strictures. The main cause of trauma is the loss of blood flow (ischemia) and resultant necrosis of the tracheal lining.

Cuff pressures are typically set between 10–50 mm Hg. This range of pressures is relatively wide and for any particular patient the formation of a seal without creating an ischemia will require holding the pressure in a much narrower range. Moreover, because tracheal tubes are used in a dynamic environment, the pressure required to maintain an adequate seal will vary. Finally, cuff pressure will vary due to the diffusion of nitrous oxide into the cuff. Thus, establishing a correct cuff pressure and correctly regulating the cuff to this pressure are both important. For example, during mechanical ventilation, the intracuff pressure must be low enough to allow tracheal capillary perfusion, thus reducing the risk of ischemia, while being high enough to prevent either loss of tidal volume or significant aspiration.

The use of high volume, low pressure endotracheal tube cuffs starting in 1973 reduced the incidence of complications from prolonged tracheal intubation. This more compliant cuff design provides a satisfactory tracheal seal for positive pressure ventilation associated with significantly lower cuff-tracheal mucosa contact pressure. Unfortunately, when lung compliance significantly decreases—as often occurs in critically ill ICU patients—high airway pressures are transmitted through the distal cuff surface during inspiration. Cuff-tracheal mucosal contact pressures approach peak airway pressures as high as 50 mm Hg during each inspiration. This contact pressure far exceeds tracheal mucosal perfusion pressure of 15 mm Hg and significant ischemic damage can occur, and in fact mucosal ischemic damage commonly occurs in observed patient populations. Endoscopic and biopsy studies suggest a high incidence of mucosal ulceration, cartilage infiltration with bacteria, and ultimately, scar formation with the development of clinically significant airway narrowing. Local mucosal defense mechanisms are inhibited during tissue ischemia, allowing bacteria to multiple and invade deeper structures.

An additional cause of cuff pressures that exceed mucosal perfusion pressure is brought about during nitrous oxide general anesthesia. Nitrous oxide diffuses into a cuff eighty times faster than nitrogen diffuses outward, producing a significant increase in cuff volume such that cuff pressures often exceed 60 mm Hg, and the above-described ischemia and deterioration of the mucosa result.

Others have recognized and proposed solutions to the problems associated with excessive cuff pressures during prolonged intubation. For example, U.S. Pat. No. 5,235,973—Levinson discloses a system for monitoring and controlling cuff pressure that requires both an inflation line and a monitoring line connected to the cuff. The monitoring line is used to determine when additional pressure should be applied to the cuff, and is governed by the pressure in the inspiration line of the ventilator. However, this system raises cuff pressure with each inspiration to avoid loss of tidal volume without regard for cuff-mucosal perfusion pressure and thus cannot provide satisfactory pressure regulation. Another pressure control system is disclosed in U.S. Pat. No. 4,924,862—Levinson. In this system, pressure relief valves connect the cuff and a source of pressurized gas. A high pressure relief valve regulates cuff over-pressure, while a low pressure relief valve is controlled by a flow detector monitoring the cuff inflation line. A continuous flow in the cuff inflation line is indicative of a cuff leak. Cuff pressure regulation via mechanical valves is disclosed by U.S. Pat. Nos. 4,770,170 and 4,825,862 both to Sato et al. However, as well known to those of skill in the art, mechanical valves have performed poorly in clinical use.

One pressure regulation device known as the Cardiff Cuff Controller has been reported in the literature. See Morris et al., J. Med. Eng. & Tech., Vol. 9, No. 5 (September/October 1985) at pp. 229–30; Cobley et al., "Endobronchial Cuff Pressures," *British J. Anesthesia,* 70:576–78 (1993). This device regulates cuff pressure using an air reservoir and pump that connect to the cuff via a controlled valve. A relief valve is also provided to alleviate over-pressure conditions. Use of this device is also reported in the literature. See Willis et al., "Tracheal tube cuff pressure: Clinical use of the Cardiff Cuff Controller," *Anethaesthesia* 43:312–14 (1988); and Cobley et al., referenced immediately above.

As explained above, the prevalence of tracheal tubes, and in particular endotracheal tubes, has led to detrimental effects being observed, particularly when patients are intubated for a long period of time. For example, pulmonary complications are caused by aspiration during prolonged orotracheal intubation. The current use of high volume, low pressure cuffs alleviates this problem to a certain extent. See Spray et al., "Aspiration Pneumonia: Incidence of Aspiration with Endotracheal Tubes," Am. J. Surg. 131:701–03 (June, 1976). However, aspiration can and does occur even using a properly designed high volume, low pressure cuff inflated to and maintained at an appropriate pressure. Regurgitated gastric fluids and pharyngeal secretions that enter the proximal trachea often accumulate above the inflated cuff and may channel to soil the more distal trachea and lungs. Physicians believe this pathway to be the most common mechanism producing hospital acquired bronchitis and pneumonia. As many as twenty-five percent (25%) of patients requiring more than several days of intubation and ventilation within an ICU develop nosocomial pneumonia. Typically, oral and pharyngeal secretions are removed by nursing personnel on an as-needed basis. However, the handheld suction catheters currently in use fail to drain the subglottic region. As much as 150–200 ml of liquid secretions have been removed over a 24 hour period in one study using once hourly manual syringe evacuation. Significant problems with thick, viscous secretions plagued prior endotracheal tubes that attempted to drain this region. Small bore suction tubing has to be replaced with much larger total volume tubing but not at the expense of greatly increasing the outer diameter of the endotracheal tube at the vocal cord level.

The literature reports a relationship between upper gastrointestinal, oropharyngeal colonization and the occurrence of pneumonia. See Mahul et al. "Prevention of nosocomial pneumonia in intubated patients: respective role of mechanical subglottic secretions drainage and stress ulcer prophylaxis," Intensive Care Med. 18:20–25 (1992). In the Mahul et al. study, both hourly drainage of subglottic secretions and the use of sucralfate or antacids as a prophylactic measure were tried as alternative methods of preventing pneumonia. The drainage of subglottic secretions was performed using a HI-LO EVAC endotracheal tube manufactured by Mallinkrodt; this tube has an elliptic dorsal opening above the cuff that is connected to a separate, integral aspiration lumen. A small bore suction channel was incorporated into the wall of the tube with its distal opening 5.0 mm above the inflated cuff. The antacid cytoprotective agent was administered via a nasogastric tube separate and distinct from the endotracheal tube. It is noted that prior study of this type of endotracheal tube by this inventor's laboratory found a high incidence of suction channel blockage with long term use. In addition, the rate and viscosity of removed secretions is greatly limited by the small lumen.

Thus, in a long term intubation subject, pathogenic bacteria multiply in the pool of secretions that accumulate above the inflated endotracheal tube cuff, providing a significant inoculum when aspirated into the distal trachea. Irrigation and drainage are the methods of choice when attempting to remove infected material from the body. Irrigation dilutes the bacterial colony count and suction drainage removes this material from the body. Applying this technique to the area below the vocal cords and above the inflated cuff (subglottic region), may reduce the incidence and amount of infected secretions that reach the lungs and therefore prevent nosocomial pneumonias. Subglottic irrigation with a bactericidal solution may also significantly decrease the infectivity of secretions that may be aspirated into the distal trachea.

For the foregoing reasons, others have attempted to construct endotracheal tubes that incorporate a suction device to draw fluids from the pharynx or a channel to irrigate a body area. U.S. Pat. No. 2,854,982 discloses a nasopharyngeal tube that comprises an outer tube surrounding a central lumen. The outer tube includes orifices for providing suction above the cuff. U.S. Pat. No. 3,593,713 discloses a device similar to the aforementioned patent but uses the outer tube to provide irrigation. U.S. Pat. No. 4,468,216 also discloses an irrigation/suction catheter with a central lumen surrounded by an outer tube. The outer tube is used to suction liquids provided via the central lumen.

Despite the above-described attempts of the prior art, however, there are currently no fully satisfactory tracheal tubes that can be left in place for long periods of time. As shown above, it is desirable to regulate the cuff pressure of a tracheal tube. Maintaining such a constant, controlled cuff pressure avoids under-inflation, and the concomitant loss of the mechanical barrier against gross spread of secretions. It is also desirable to avoid over-inflation and thus avoid ischemic mucosal damage that inhibits the local host defenses against infection. It is further desirable to prevent the distal spread of infected subglottic secretions. Toward this end, the subglottic region should be drained and it is further desirable to dilute the bacterial inoculum by irrigation and possibly with bactericidal medication and to frequently remove this material by suction, prior to channeling around the inflated cuff. As explained above, the combination of recurrent regurgitation from the gastrointestinal tract and recurrent liquid aspirations produce a situation that could overwhelm the defense mechanism of the patient, producing nosocomial pneumonia. However, these steps will reduce the incidence of both nosocomial pneumonia and irritation of the mucosa.

It is therefore an object of the present invention to provide methods and apparatus for intubating a patient that simultaneously irrigates the subglottic region with saline or a bactericidal solution, frequently drains the subglottic secretions by controlled suction, and by servoregulating cuff pressure over a very narrow range. It is a further object of the present invention to provide such methods and apparatus in a form that is simple and efficient, and that can be easily manufactured.

SUMMARY OF THE INVENTION

It has now been found that the problems discussed above are overcome by providing a coordinated system that improves the mechanical barrier against aspiration. A modified endotracheal tube comprising an airway lumen defined by an outer wall with an inflatable cuff disposed around the outer wall and connected to a cuff pressure line that also includes a subglottic suction lumen having a distal end terminating at an opening proximal of the inflatable cuff, and an irrigation lumen having a distal end terminating at an opening proximal of the inflatable cuff. In preferred embodiments of the present invention either the cuff pressure line, or irrigation lumen may be integral with the outer wall of the tracheal tube. In certain preferred embodiments, one or both of the subglottic suction lumen and the irrigation lumen are concentric with the airway lumen. In other preferred embodiments, the distal ends of the cuff pressure line, the subglottic suction lumen, and the irrigation lumen are all terminated by a connector, such as those familiar to those of skill in the art. The apparatus disclosed herein is most preferably incorporated into endotracheal tubes.

Thus, the present invention discloses a system for intubating a patient that uses a tracheal tube having an airway lumen connected to a source of gas to be administered to the respiratory system of a patient, an inflatable pressure cuff disposed around the outer wall of the airway lumen, and connected to a cuff pressure line that is in turn connected to a source of pressurized fluid and a fluid pressure regulator. The tracheal tube of this embodiment also includes a subglottic suction lumen having a distal end terminating at an opening proximal of the inflatable cuff and a proximal end connected to a vacuum source and an irrigation lumen having a distal end terminating at an opening proximal of the inflatable cuff and a proximal end connected to a source of irrigation fluid. Preferably, the pressure regulator maintains a preselected cuff pressure between 10 and 30 mm Hg, and most preferably about 15–20 mm Hg. In certain embodiments, the fluid pressure regulator comprises a compressor connected to a reservoir that connects to the cuff pressure line and a pneumatic relief valve disposed between the compressor and the reservoir. Additionally, in other embodiments, the subglottic suction lumen is connected to an automatic suction device, which preferably applies suction for a predetermined period of time at predetermined intervals. The irrigation lumen is preferably connected to an automatic perfusion pump, and it is further preferred that the automatic perfusion pump distributes fluid through the irrigation lumen for a predetermined period of time at predetermined intervals.

The present invention also discloses methods of intubating a patient.

Thus, a modified endotracheal tube has been developed that provides a means to deliver an irrigating solution to the subglottic region and a specialized outer sleeve that directs significant suction drainage to the area above the inflated cuff. A standard endotracheal tube having a curved, thick-walled shaft, a proximal connector, and a distal inflatable high-volume, low pressure cuff with associated inflation channel and pilot valve, has been modified to provide an irrigation channel in the concave side of the shaft wall with its proximal end consisting of a leur lock connector and its distal end opening immediately above the inflated cuff. A suction channel has been incorporated around the outside surface of the endotracheal tube shaft consisting of a compliant, thin walled sleeve that tapers from the proximal to the distal end. The sleeve is preferably approximately 8.0 mm wider than the tube shaft in the most proximal location with a gradual taper only 1.0 mm wider at the distal attachment. The sleeve is attached immediately above the inflated cuff, with rounded edges to prevent tissue trauma. The compliant nature of the sleeve provides a large area for suction but molds to the glottic tissues, thereby minimally increasing the outer diameter of the endotracheal tube at the vocal cord level. Laboratory study suggests 0.30 mm PVC plastic to be a satisfactory material for this use. The proximal sleeve is attached to a large bore suction catheter, (preferably greater than 6 French) such that the entire inside circumference of the sleeve easily drains. Similarly, tracheostomy tubes can be modified in accordance with the present invention to include an outer sleeve that provides connection to a suction and/or irrigation control device. Additionally, in any embodiment, the present invention can be connected to a battery-powered suction and/or irrigation device for ambulatory use.

The present invention also includes an electromechanical device that regulates and coordinates each function of the modified endotracheal tube. A simple volume regulated infusion pump is used to deliver a controlled amount of non-viscous liquid to the irrigation channel of the endotracheal tube. The infusion may be adjusted from 0 to 30 ml/hr and will be abruptly stopped if cuff pressure or suction pressure are lost. Subglottic suction is regulated by a device that down-regulates wall suction from 300 mm Hg to an adjustable suction of 0–150 mm Hg. A timing device, powered by the force of wall suction, will regulate the on-off cycle. A short period of suction will be followed by several minutes of silence. Suction from this device will be directed through the subglottic suction catheter, down the sleeve, to the area above the inflated cuff.

Finally, it is preferred that cuff pressure is closely regulated by an electronic servomechanism that maintains pressure near a preselected value. This servomechanism quickly adjusts cuff pressure over a wide range of clinical environments such as positive pressure ventilation with high airway pressures, coughing, and during the changing volumes associated with nitrous oxide anesthesia. Unique to the present invention is a very rapid and accurate electronic valve solenoid that can adjust cuff pressure within 0.30 seconds without overshoot. This allows attenuation of elevated cuff pressure that always occurs when high inspiratory airway pressures are transmitted through the underside of the inflated cuff. In certain embodiments, the pressure regulator maintains a preselected pressure in the range of 10–50 mm Hg, and most preferably below mucosal perfusion pressure of 15 mm Hg. This device consists of an air compressor, electronically controlled pneumatic relief valve, and a non-compliant reservoir. Output from this pressure regulator is attached to the pilot valve of the cuff inflation channel.

DETAILED DESCRIPTION OF THE PREFERRED EMBODIMENTS

Figure 1:
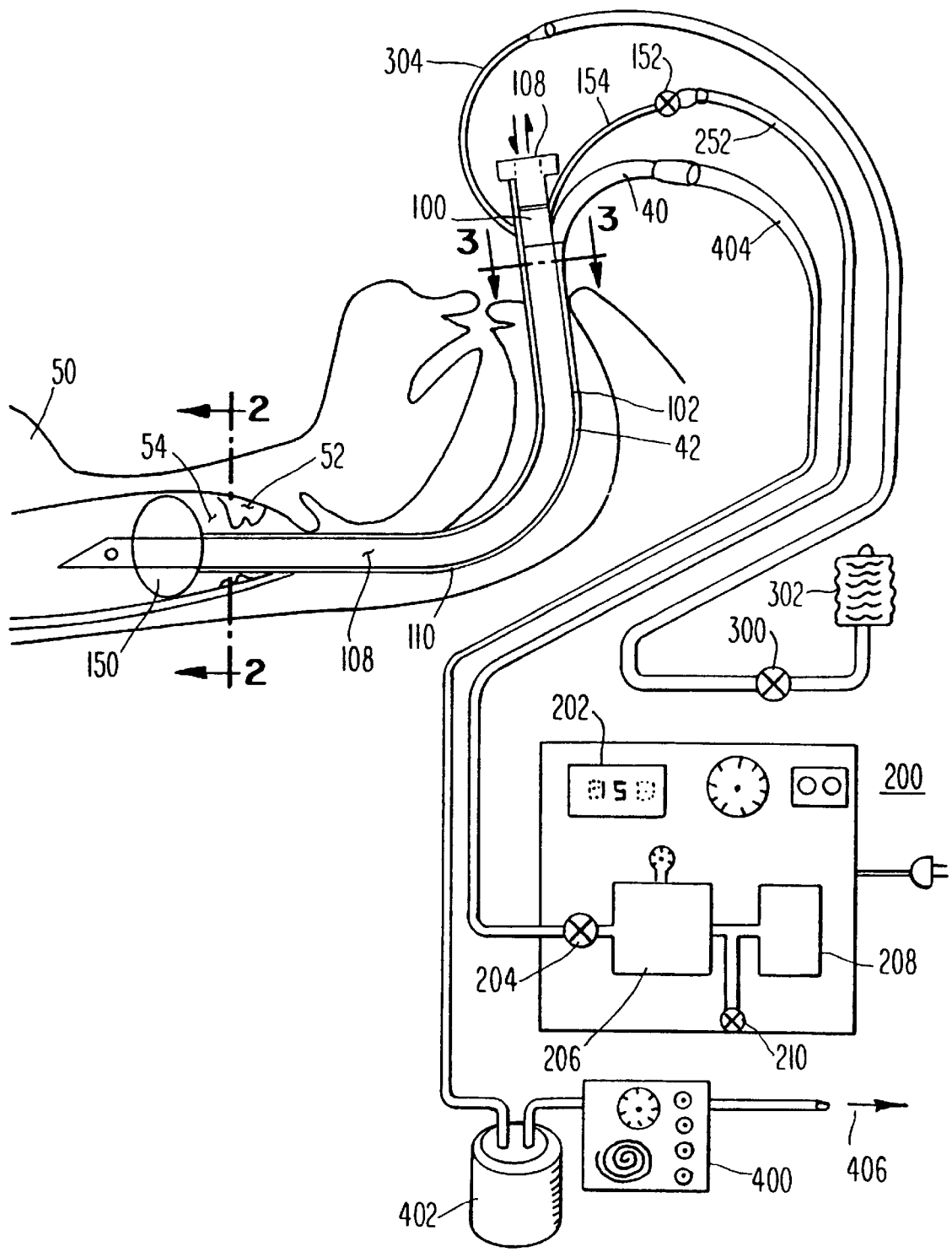
FIG. 1 is a partially schematic, partially diagrammatic illustration of the system of the present invention.

Referring to FIG. 1, there is shown a partially schematic, partially diagrammatic illustration of the system of the present invention. A patient 50, illustrated in cross-section through the median plane, is nasally intubated sing a tracheal tube 100 made in accordance with the present invention. The area below the vocal cords 52, and above the inflated cuff 150 is defined as the subglottic region 54.

Figure 2:
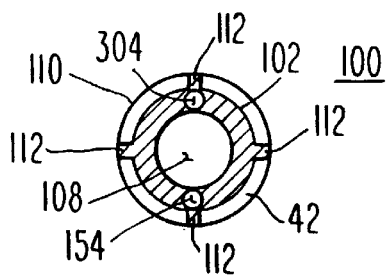
FIG. 2 is a cross-section of a preferred embodiment of the distal tracheal tube of the present invention, taken along lines 2—2 in FIG. 1.
Figure 3:
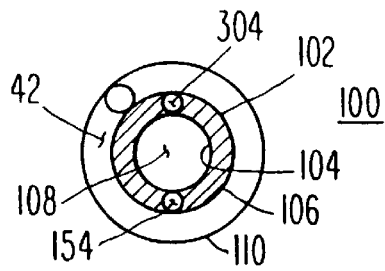
FIG. 3 is a cross-section of a preferred embodiment of the proximal tracheal tube of the present invention, taken along lines 3—3 in FIG. 1.

As seen in FIGS. 1–3, the tracheal tube 100 comprises an airway lumen 108 in a compliant shaft 102 defined by an inner wall 104 and an outer wall 106. As well known to those of skill in the art, this lumen 102 permits fluids to be transferred into and out of the airways of the patient 50. Surrounding the outer wall 106 is an inflatable cuff 150 and a thin-walled, compliant sleeve 110 circumferential with the shaft 102. Most preferably, the proximal end is 8.0 mm wider than the outer shaft wall 106. This sleeve 110 gradually tapers to a width 1.0 mm greater than the outer shaft wall 106. As seen in FIG. 2 at its distal end, the outer sleeve 110 attaches to the outer shaft wall 106 at four equally spaced points 112, i.e., 3, 6, 9, and 12 o'clock. This attachment is located approximately 2.0 mm above the inflated cuff 150. Incorporated into the convex wall of the shaft is the cuff inflation channel 154 terminating into the inner atmosphere of the cuff 150. The inflatable cuff 150 is thus attached by a line 154 to the cuff pressure regulator line 252 via a pilot valve 152.

As also seen in FIG. 1, the cuff pressure line 252 is connected to a cuff pressure regulator system 200 via a pilot valve 152. The servoregulator 200 most preferably includes a compressor 208, connected to a reservoir 206. A pneumatic pressure relief valve 210 disposed between the compressor 208 and the reservoir 206 regulates the pressure in the reservoir 206. The cuff pressure servoregulator 204 also preferably includes a numerical display 202 that permits the user to visually determine the pressure being delivered to the cuff 150. The cuff pressure servoregulator 204 includes feedback circuits and sensors that compare the pressure sensed to the predetermined pressure set by an operator. If the pressure is too low, additional gas is permitted to flow to the cuff 150, either by release from the reservoir 206 or by operating the compressor 208. If the pressure exceeds a predetermined maximum, pressure is relieved by allowing gas to escape from the pneumatic relief valve 210.

Most preferably, the pressure servoregulator 204 comprises an electronic servomechanism that autoregulates cuff pressure in the range of 0–60 mm Hg, although it is preferred that the predetermined pressure be set between 10–30 mm Hg, and most preferably between about 15–20 mm Hg. Cuff-tracheal mucosal contact pressure (approximate to cuff pressure) greater than 15 mm Hg has been shown to significantly decrease tissue perfusion. The present invention most preferably uses equipment that can regulate the predetermined pressure within about ±2.0 mm Hg. Pressure regulation will occur within 0.30 seconds of detecting a change from baseline. This will attenuate cuff pressure increases transmitted during the inspiratory phase of positive pressure ventilation. This fast and accurate servoregulation is unique to the electronic methods described in the present invention. In use, the lowest pressure that provides a seal during positive pressure ventilation should be used. In preferred embodiments, air is added to the cuff 150 by an electronically controlled pneumatic valve 204 disposed between the cuff 106 and the reservoir 206.

One device that can be adapted to regulate pressure in accordance with the present invention is the A.T.S.™ 1500 Tourniquet System manufactured by Aspen Labs, a subsidiary of Zimmer, Dover, Ohio (U.S.A.). This device regulates the pressure of tourniquets, but can be readily adapted for use in accordance with the present invention. Those of skill is the art will realize that the Zimmer system or other such systems can be easily programmed in accordance with the parameters set forth above and used in a system such as that described and illustrated herein.

As best illustrated in FIG. 2, the tracheal tube 100 of the present invention also includes an irrigation channel 304 preferably incorporated into the wall of the thick walled, curved flexible shaft 102. The irrigation channel 304 delivers non-viscous liquids to the subglottic region 54. The irrigation channel 304 is connected to a liquid reservoir 302 and volume infusion pump 300. This irrigation is useful to prevent drying of the mucosa or for delivery of bactericidal medication to the region. It is preferred that the irrigation system of the present invention delivers non-viscous liquids to the subglottic regions such as dilute antibiotic solutions that provide a chemical barrier to infection. Alternatively irrigation with local anesthetic solutions that provide a field numbing block of the trachea for patient comfort may be useful. Preferably, the liquid is delivered at a rate of about 0–20 ml/hr. It is also preferred that the delivery of the liquid is integrated with the intermittent suction described above.

As explained above, a thin walled, compliant outer sleeve 110 surrounds the outer wall of the endotracheal tube shaft 102. This outer shaft tapers in a proximal to distal direction forming a suction lumen 42 with a 8.0 mm width near the proximal end and a 1.0 width near its distal end. The tapered and compliant nature of this sleeve at body temperature allows a large suction channel without the need to greatly enlarge the outside diameter of the endotracheal tube at the vocal cord level. Most preferably, the distal end of the subglottic suction lumen 42 terminates at an opening immediately proximal of the inflatable cuff 150. A large bore suction catheter 40 is attached to the proximal end of the subglottic suction channel 42 such that fluids easily drain from the entire circumference of the channel. This suction catheter is connected to a suction canister 402 and suction regulatory device 400 that down-regulates wall suction 406 for delivery to the subglottic region.

Among other advantages, this design permits the suction applied to the subglottic suction lumen 42 to provide suction around the periphery of the annular space between the tracheal lining and the outer wall of the tracheal tube 100. Additionally, an annular orifice such as that shown in FIG. 2 is less likely to be occluded during suction. The suction lumen 42 is integrated into a tubular proximal extension, shown in FIG. 1, that includes a connector 404 that connects the suction lumen 42 to a subglottic suction regulator 400. Preferably, a canister 402 for removing aspirated fluids is provided and the suction regulator 400 is connected to a source of suction 406 through a timer. Typically, wall suction 406 is provided at 300 mm Hg, which is most preferably down regulated to a maximum of 150 mm Hg. The timer permits the application of suction to be intermittent.

Figure 4:
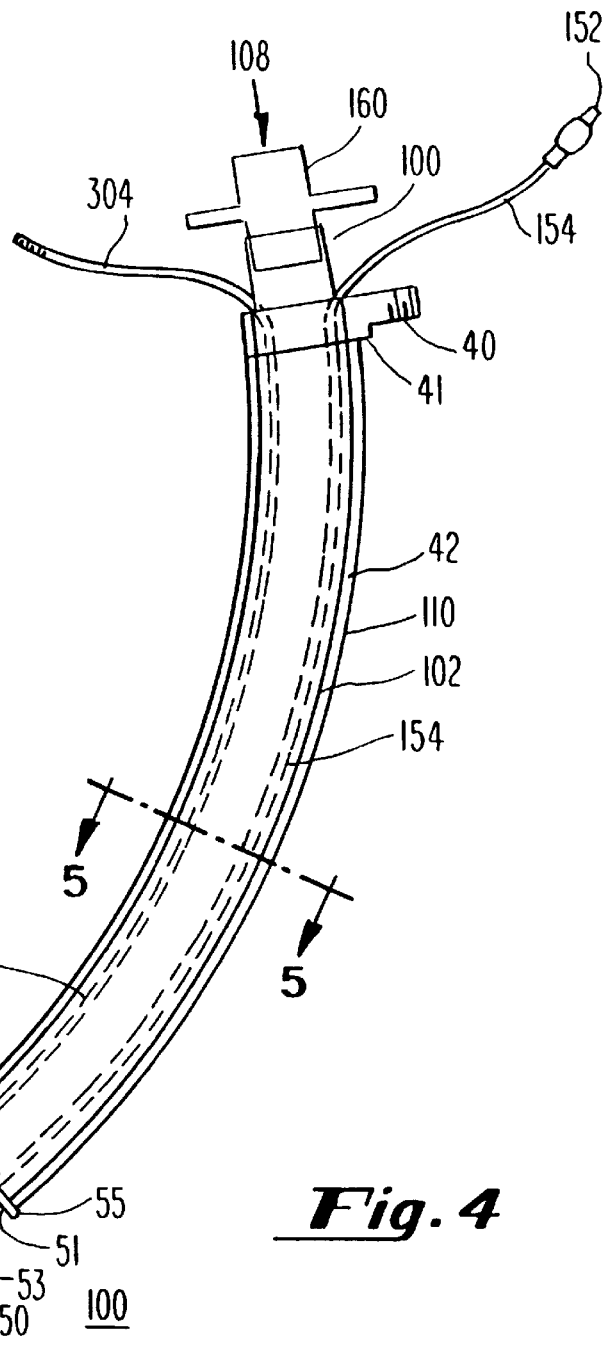
FIG. 4 illustrates a subglottic suction endotracheal tube for irrigation and suction; having a flexible outer sleeve.

Referring now to FIG. 4, further details of an endotracheal tube for subglottic suction having a flexible outer sleeve and irrigation suction channels are illustrated. Like reference numerals illustrate like features described above with reference to FIGS. 1–3. In FIG. 4, an air tight connection 41 disposed at the proximal end of the endotracheal tube is illustrated. The proximal end of the device includes a connector 160.

As explained above, the present invention provides suction to the subglottic space, illustrated above with reference to FIG. 1. In FIG. 4, it is seen that the distal end of the outer flexible sleeve 110 includes a collar or shoulder 55 that has rounded edges. Also illustrated is the opening 51 that is created between the walls of the compliant outer sleeve 110 and the tubing that forms the suction lumen, which is an annular space. FIG. 4 also illustrates the opening 53 that permits the inflation line 154 to communicate with the inflatable cuff 150 in preferred embodiments. Finally, at the distal end of the device 100, an opening known in the art as a "Murphy eye" is illustrated.

Figure 5:
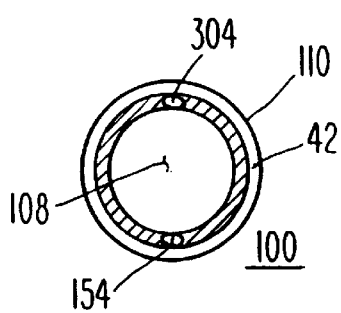
FIG. 5 is a cross-sectional view of the endotracheal tube shown in FIG. 4 taken along lines 5—5.

FIG. 5 illustrates a cross-section taken along lines 5—5 of FIG. 4. As explained above with reference to FIGS. 2–3, devices made in accordance with the present invention contain several lumens within one set of tubing. In this embodiment, the irrigation channel 304 and the inflation channel 154 are disposed at the top and bottom of the cross section, respectively. The airway lumen 108 is surrounded by the tubing that contains the irrigation channel 304 and inflation channel 154, and an annular suction lumen 42 surrounds this structure. The outer wall is defined by the compliant outer sleeve 110, as explained above.

Figure 6:
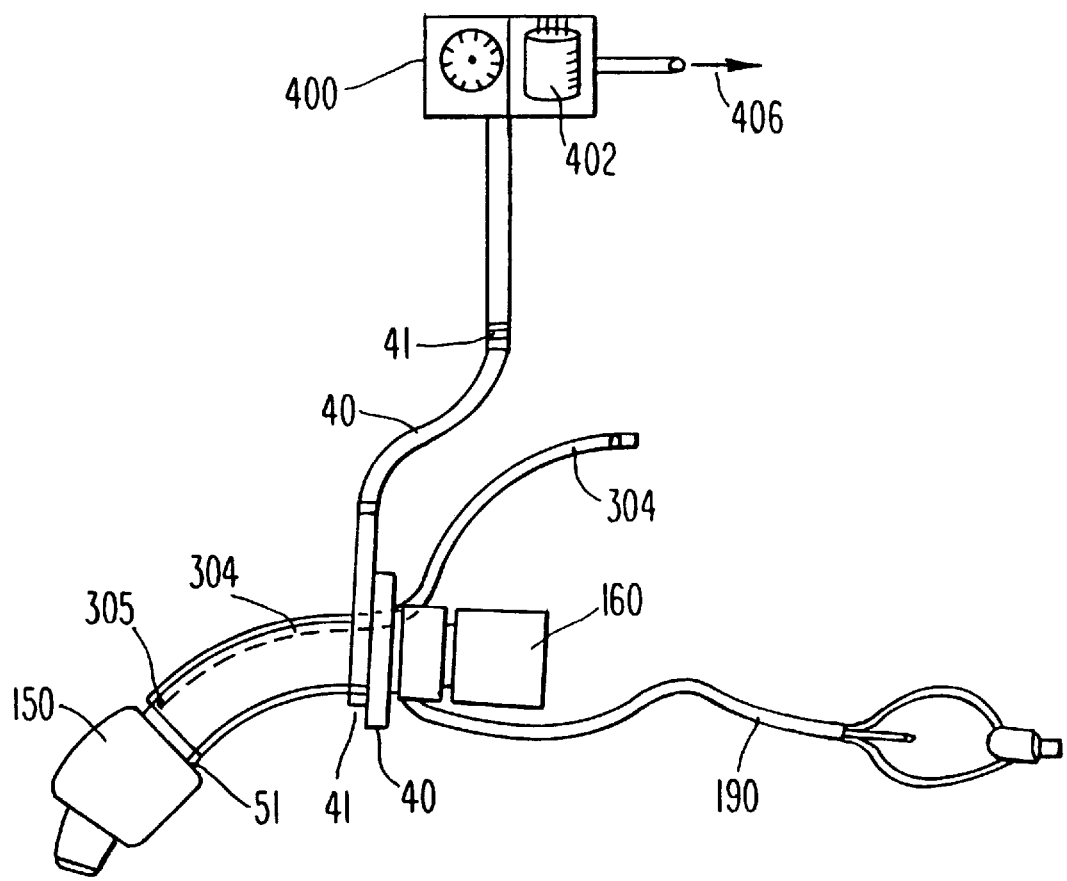
FIG. 6 is an illustration of a subglottic suction tracheostomy tube with an outer flexible sleeve made in accordance with the present invention.

An alternate embodiment in the present invention is illustrated in FIG. 6. In this illustration, like reference numerals are used to denote like structure that has been described above with reference to FIGS. 1–5. In FIG. 6, a subglottic suction tracheostomy tube is shown which includes an outer flexible sleeve and irrigation and suction channels, substantially as described above. In this embodiment, an inflatable cuff 150 is again disposed near the distal end of the device, and an opening 51 between the inflatable cuff 150 and the annular lumen used for suction is provided such that the opening will be disposed in the subglottic region. The suction channel in this embodiment is connected to a suction catheter 40 which preferably is connected to a suction regulatory device 400 (described above) using a modular connection such as a leur lock 41. In this embodiment, it is preferable that the wall suction provided is between about 250–300 mg/Hg, which is regulated between 0–150 mg/Hg with a timing wherein the suction is applied for about 20 seconds and a dwell where no suction is supplied of about 60 seconds.

FIG. 6 also illustrates a pilot balloon 190 extending distally from the device, and in this embodiment the connector 160 at the proximal end is preferably a 15 mm connector, as known in the art.

Figure 7:
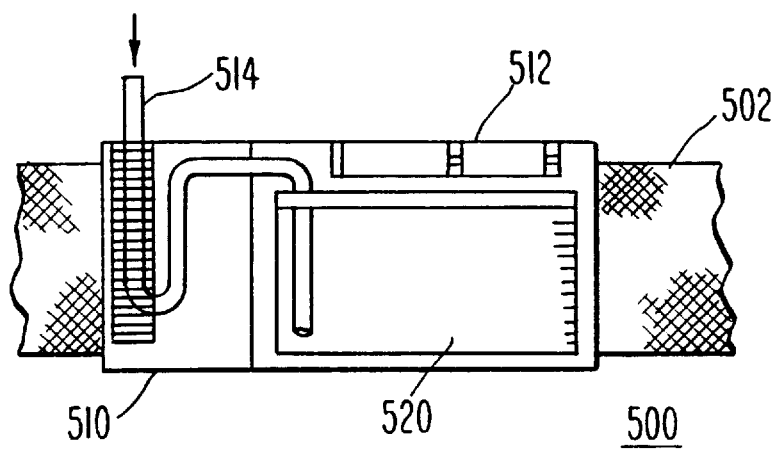
FIG. 7 depicts a battery-powered suction pump for use in conjunction with the present invention.

FIG. 7 provides a partially schematic illustration of a belt-worn battery pack 500 that can be used with the embodiments in the invention described above. The battery pack 500 is preferably worn by the patient on a belt 502 and includes a miniature suction pump 510 that is operated by batteries 512. The miniature suction pump is connected to tubing 514 and the tubing 514 transfers any fluids that are aspirated into a suction canister 520, which is most preferably a disposable device.

The present invention thus also discloses improved methods of intubating a patient. In use, the methods of the present invention require inserting a tracheal tube into the patient and inflating an inflatable pressure cuff to a predetermined pressure while regulating the pressure in the inflatable pressure cuff. During intubation, fluid such as anesthetic gas moves through the tracheal tube and into the patient. As described above, the methods of the present invention also include applying suction to a subglottic secretion suction lumen, and irrigating a region by flowing a liquid through an irrigation lumen. By using such improved methods, extended period of intubation can now be effectively achieved while minimizing any related trauma or other adverse conditions.

Although certain embodiments of the present invention have been disclosed herein and described with particularity, these embodiments are intended to illustrate the function and operation of the present invention and are not intended to act as limitations. Upon review of the foregoing description, those of skill in the art will immediately apprehend useful modifications, adaptations and alternate embodiments that utilize the spirit of the present invention. Accordingly, in order to determine the full scope of the present invention, reference should be made to the appended claims.

It is claimed:

1. An integrated system providing an improved mechanical and chemical barrier against the spread of acidic or infected secretions into the distal trachea comprising an endotracheal tube, wherein the endotracheal tube comprises:

a thin walled, compliant outer sheath; defining a suction channel concentric with an outer wall of the endotracheal tube for removing acidic or infected secretions from a subglottic region below the vocal cords and above an inflated cuff, the outer sheath terminating immediately above the inflated endotracheal tube cuff; and an irrigation channel integral with the outer wall for delivering a non-viscous liquid to the subglottic region for tissue hydration and the dilution of bacterial inoculum, used in combination with an outer sleeve suction channel to provide a mechanical irrigation and drainage of the subglottic region in a manner similar to surgical management of an infected body space, whereby topical delivery of an antibiotic and antifungal solution to the subglottic region provides a chemical barrier against the distal spread of infected secretions, thereby significantly decreasing the number of bacteria and the degree of infectivity of those liquid secretions that pass the inflated cuff, and further, the irrigation channel also provides for the irrigation and drainage of a dilute solution of topical local anesthetic, whereby the local anesthetics produce a numbing field block for awake intubated patients, thereby providing an integrated system for the topical delivery of therapeutic medication requiring rapid access to a highly vascular mucous membrane, such as antihypertensive and antianginal medications, the system further comprising an electronic and mechanical control device for regulating and integrating irrigation, suction, and cuff pressure, wherein subglottic irrigation will cease if suction or cuff pressure regulation malfunction and wherein an alarm condition is indicated if any one of irrigation, suction and cuff pressure regulation are not functional.

2. The system of claim 1, wherein the tracheal tube is a pliable, curved shaft with an open distal end and a proximal end comprising of a standardized connector for attachment to a ventilator circuit.

3. The system of claim 1, wherein the cuff inflation channel is integral with the wall of the shaft on the convex side of the endotracheal tube, a distal opening in said channel lying within a high-volume, low pressure endotracheal tube cuff, and a proximal end thereof comprising flexible tubing that connects with a pilot balloon and an inflation valve connected to a cuff pressure regulator line of the control device.

4. The system of claim 1, wherein the irrigation channel is integral with the wall on the concave side of the endotracheal tube to a point ending immediately above the inflated cuff and the proximal end comprises flexible tubing that connects with a pump infusion line.

5. The system of claim 1 wherein the irrigation channel is combined with the outer sleeve suction channel and alternately delivers a non-viscous liquid to the subglottic space using a timing mechanism to alternate between irrigation and suction through one common channel.

6. The system of claim 1, wherein the outer sleeve is concentric with the outer wall and forms a suction channel wider at a proximal attachment point as compared to its width at a distal attachment point, the outer sleeve being attached to the shaft at a location immediately above the inflated cuff; the sleeve comprised of flexible material such that it substantially conforms to the shape of the glottis and vocal cord structures at body temperature, whereby a significant increase in the total outer diameter of the endotracheal tube at the vocal cord level is prevented, such that the sleeve indents at the vocal cord level only to extend outward in the other directions, thereby providing a large surface area for applied suction; wherein at the distal attachment, the sleeve is approximately 1.0 mm wider than the outer wall of the shaft in all directions; the distal openings provide a large area for applied suction such that viscous secretions can be removed with ease; the outer sleeve having a reverse taper to a width approximately 8.0 mm wider than the outer wall of the shaft at its proximal attachment; and a large bore flexible suction catheter connected within a proximal portion of the suction channel for providing unimpeded liquid flow, the proximal connection formed in an airtight seal between the outer sleeve and the proximal endotracheal tube wall, whereby the semi-rigid connection of the sleeve to a suction catheter provides for efficient suction drainage of the entire proximal subglottic suction channel, wherein the flexible suction catheter is of a short length and connects via a connector to a large bore suction line from a suction control device.

7. The system of claim 1 wherein the outer sleeve suction channel is connected to a stethoscope to listen for an air leak around the inflated cuff, thereby providing for an accurate diagnosis of level of cuff inflation pressure required to produce a tight seal.

8. The system of claim 7, wherein the cuff is modified fenestrated cuff used in chronic tracheostomy, whereby the cuff and the outer sleeve suction channel transmit air pulses from the distal tracheal to an external environment, producing sounds and words for communication.

9. The system of claim 1, wherein the tracheal tube is an endotracheal tube for providing a patient airway for aspiration protection and for the delivery of respiratory gases and anesthetics in the care of patients.

10. The system of claim 9, including a standard endotracheal tube that functions as a channel for the intermittent suctioning of secretions from the distal trachea and proximal bronchi.

11. The system of claim 1, wherein the liquid infusion device comprises a reservoir attached to a volume infusion pump for infusing a non-viscous liquid at a rate between 0–30 ml/hour through an output connected to the flexible tubing of the subglottic irrigation channel of the endotracheal tube.

12. The system of claim 1, wherein the cuff pressure autoregulator comprises: an air compressor; a gas reservoir; a pneumatic control valve; an electronic pressure transducer and servoregulator; a digital display; and an electronic alarm system, wherein the air compressor provides cuff pressure control within about 0.30 seconds of a change in pressure to a pressure within 2.0 mm Hg of a desired pressure in the range of 0–60 mm Hg, with a default pressure of about 15 mm Hg, whereby compressed gas from the reservoir travels through a cuff pressure control line to connect with a cuff inflation channel in the endotracheal tube.

13. The system of claim 12, further comprising a rapid gas infusion system and an electronically controlled, rapidly acting pneumatic valve and servo mechanism that maintains a constant cuff pressure despite external influences such as positive pressure ventilation, coughing, bucking, and following interventional procedures such as ventilation with nitrous oxide.

14. The system of claim 1, wherein the suction channel is connected to wall suction that is down-regulated to an adjustable pressure of about 150 mm Hg and further comprises a mechanical timer for timing control of suction activation and quiescence, whereby suction is activated for a period of about 15–60 seconds followed by a several minute period of quiescence; and further connect a suction canister.

15. The system of claim 13, wherein pressure sensors within the suction control device recognize an acute rise in suction pressure indicating viscous secretions or mucosal tissue caught within the opening of the suction channel, whereby the control device will transiently increase suction pressure to relieve the obstruction, followed by termination of applied suction if the channel remains significantly occluded, and providing an audible alarm condition.

16. The system of claim 15, wherein the suction canister contains a port to withdraw and test secretions removed from the subglottic space for the presence of gastric acid, presence of GI tube feedings, and to obtain material for gram stain and culture of infected secretions, thereby providing the diagnosis of recurrent GI reflux, and bacterial colonization of the hypopharynx.

17. The system of claim 1, wherein electronics integrate the function of the system such that liquid infusion is halted if cuff pressure or suction pressure are lost, and wherein electronic alarms provide assurance to the proper function of the system.

18. A system for intubating a patient with a tracheal tube having a proximal and a distal end and having an inflatable cuff disposed near the distal end of the tracheal tube, a subglottic suction lumen having a distal end terminating at an opening proximal of and superior to the inflatable cuff, and an irrigation lumen having a distal end terminating at an opening proximal of and superior to the inflatable cuff, comprising:

a cuff pressure regulator for controlling the pressure in the inflatable cuff and having a compressor and a relief valve adaptable to be in flow communication with the inflatable cuff and an electronic pressure regulator adaptable to cycle the compressor and supply pressure to the cuff if pressure within the cuff is less than a predetermined minimum pressure and open the relief valve if pressure within the cuff exceeds a predetermined maximum pressure;

a suction regulator, for controlling the suction through the subglottic suction lumen that is adaptable to suction in a suglottic region exterior to the tracheal tube and proximal to the inflatable cuff, the suction regulator having a pump in flow communication with the subglottic suction lumen; and a control device for regulating and integrating irrigation through the irrigation lumen, suction through the subglottic suction lumen, and cuff pressure in the inflatable cuff, wherein subglottic irrigation will cease if suction or cuff pressure regulation malfunction and wherein an alarm condition is indicated if any one of irrigation, suction and cuff pressure regulation are not functional.

19. The system of claim 18, wherein the cuff pressure regulator maintains a predetermined cuff pressure between 10 and 30 mm Hg.

20. The system of claim 18, wherein the cuff pressure regulator maintains a predetermined cuff pressure of about 15–20 mm Hg.

21. The system of claim 18, further comprising a pressure reservoir in fluid communication with the inflatable cuff, wherein the cuff pressure regulator controls the pressure in the pressure reservoir.

22. The system of claim 18, wherein the subglottic suction lumen is connected to an automatic suction device.

23. The system of claim 22 wherein the automatic suction device applies suction for a predetermined period of time at predetermined intervals.

24. The system of claim 18 wherein the irrigation lumen is connected to an automatic perfusion pump.

25. The system of claim 24 wherein the automatic perfusion pump distributes fluid through the irrigation lumen for a predetermined period of time at predetermined intervals.

26. A method of intubating a patient comprising the steps of:

inserting a tracheal tube having an outer wall, a distal end and an inflatable pressure cuff near the distal end into the patient;

inflating the inflatable pressure cuff to a predetermined pressure;

regulating the pressure in the inflatable pressure cuff;

applying suction with a subglottic suction lumen disposed between the outer wall of the tracheal tube and a compliant outer sleeve disposed around the outer wall of the tracheal tube, the sleeve having a distal end at a point proximal to the inflatable cuff, thereby forming an opening between the outer wall and the sleeve at the distal end of the compliant outer sleeve; and irrigating a region superior to the inflatable cuff by flowing a liquid through an irrigation lumen contained within the tracheal tube.

27. The method of claim 26, further comprising the step of monitoring either the suction pressure within the subglottic suction lumen or the pressure within the inflatable cuff and regulating the irrigation through the irrigation lumen in response to said monitoring.

28. A tracheal tube having a proximal end and a distal end, comprising:

an airway lumen defined by an outer wall, an inflatable cuff disposed near the distal end of the tracheal tube and around the outer wall and connected to a cuff pressure line;

a subglottic suction lumen disposed between the outer wall of the airway lumen and a compliant outer sleeve surrounding the outer wall, the sleeve terminating at a distal end to form an annular opening between the sleeve and the outer wall of the airway lumen proximate to the inflatable cuff; and an irrigation lumen having a distal end terminating at an opening proximal of and superior to the inflatable cuff.

29. The tracheal tube of claim 28, wherein the cuff pressure line is integral with the outer wall.

30. The tracheal tube of claim 28, further comprising an air tight connection disposed near the proximal end of the tracheal tube, wherein a proximal end of the subglottic suction lumen terminates in the air tight connection.

31. The tracheal tube of claim 28, wherein the irrigation lumen is integral with the outer wall.

32. The tracheal tube of claim 28 wherein the cuff pressure line and the irrigation lumen are integral with the outer wall.

33. The tracheal tube of claim 28 wherein the cuff pressure line has a distal end terminated by a connector, the subglottic suction lumen has a distal end terminated by a connector, and the irrigation lumen has a distal end terminated by a connector.

34. The tracheal tube of claim 30, further comprising a suction channel, connected to the air tight connection, wherein the suction channel is in flow communication with the subglottic suction lumen.

35. The tracheal tube of claim 28 wherein the tracheal tube is an endotracheal tube.

36. A system for intubating a patient, comprising:

(a) a tracheal tube having a distal end and a proximal portion and an outer wall, comprising, an inflatable cuff disposed near the distal end of the tracheal tube and around the outer wall of the tracheal tube;

a compliant outer sleeve, extending from the proximal portion of the tracheal tube to a point proximate of the inflatable cuff and having a distal end, the outer sleeve being disposed around the outer wall of the tracheal tube and terminating at the distal end of the outer sleeve in an opening that defines an annulus between the outer wall of the tracheal tube and the compliant outer sleeve, and wherein a subglottic suction lumen is thereby defined between the compliant outer sleeve and the outer wall of the tracheal tube;

an airway lumen extending to the distal end of the tracheal tube and extending through the inflatable cuff;

an irrigation lumen having a distal end terminating at an opening proximal of and superior to the inflatable cuff;

(b) a pressure regulator in flow communication with the inflatable cuff;

(c) a suction regulator in flow communication with the subglottic suction lumen; and (d) a control device for regulating and integrating irrigation through the irrigation lumen, suction through the subglottic suction lumen, and cuff pressure in the inflatable cuff, wherein subglottic irrigation will cease if suction or cuff pressure regulation malfunction and wherein an alarm condition is indicated if any one of irrigation, suction and cuff pressure regulation are not functional.

37. The system of claim 36, further comprising a pressure reservoir in fluid communication with the inflatable cuff, wherein the cuff pressure regulator controls the pressure in the pressure reservoir.

38. An improved tracheal tube, having a proximal portion and a distal end, comprising:

(a) an outer tracheal wall extending from the proximal portion to the distal end of the tracheal tube;

(b) an inflatable cuff located near the distal end of the tracheal tube;

(c) an airway lumen within the tracheal tube extending through the inflatable cuff and to the distal end of the tracheal tube;

(d) a compliant outer sleeve, extending from the proximal portion of the tracheal tube to a point proximate of the inflatable cuff and having a distal end, the outer sleeve being disposed around the outer wall of the tracheal tube and terminating at the distal end of the outer sleeve in an opening that substantially defines an annulus between the outer wall of the tracheal tube and the outer sleeve, and wherein a subglottic suction lumen is thereby defined between the outer sleeve and the outer wall of the tracheal tube.

39. The tracheal tube of claim 38, further comprising an irrigation lumen extending from the proximal portion of the tracheal tube to an aperture in the outer tracheal wall proximal to the inflatable cuff.

40. The tracheal tube of claim 38, further comprising a cuff pressure channel extending from the proximal portion of the tracheal tube to the inflatable cuff.

41. The tracheal tube of claim 38, further comprising an air tight connection disposed near the proximal end of the tracheal tube, wherein a proximal end of the subglottic suction lumen terminates in the air tight connection.

42. The tracheal tube of claim 41, further comprising a suction channel, connected to the air tight connection, wherein the suction channel is in flow communication with the subglottic suction lumen.

43. A method for intubating a patient, comprising the steps of:

(a) inserting a tracheal tube having a proximal portion and a distal end into the patient, the tracheal tube comprising:

(i) an outer tracheal wall extending from the proximal portion of the tracheal tube to the distal end of the tracheal tube;

(ii) an inflatable cuff located near the distal end of the tracheal tube;

(iii) an airway lumen within the tracheal tube extending through the inflatable cuff and to the distal end of the tracheal tube;

(iv) a compliant outer sleeve, extending from the proximal portion of the tracheal tube to a point proximate of the inflatable cuff and having a distal end, the outer sleeve being disposed around the outer wall of the tracheal tube and terminating at the distal end of the outer sleeve in an opening that substantially defines an annulus between the outer wall of the tracheal tube and the outer sleeve, and wherein a subglottic suction lumen is thereby defined between the outer sleeve and the outer wall of the tracheal tube;

(b) inflating the inflatable cuff; and (c) suctioning fluids from a point proximal to the inflated cuff through the subglottic suction lumen.

44. The method of claim 43, wherein the tracheal tube further comprises an irrigation lumen having a distal end proximate and superior to the inflatable cuff, and the method further comprises the step of providing irrigation fluid through the irrigation lumen to a subglottic region proximal to the inflated cuff.

45. The method of claim 44, further comprising the step of monitoring either the suction pressure within the subglottic suction lumen or the pressure within the inflatable cuff and regulating the irrigation through the irrigation lumen in response to said monitoring.

* * * * *